United States Patent
Jia et al.

(10) Patent No.: US 7,855,242 B2
(45) Date of Patent: Dec. 21, 2010

(54) DENTAL RESIN COMPOSITION, METHOD OF MANUFACTURE, AND METHOD OF USE THEREOF

(75) Inventors: Weitao Jia, Wallingford, CT (US); Shuhua Jin, Wallingford, CT (US)

(73) Assignee: Pentron Clinical Technologies LLC, Wallingford, CT (US)

( * ) Notice: Subject to any disclaimer, the term of this patent is extended or adjusted under 35 U.S.C. 154(b) by 737 days.

(21) Appl. No.: 11/469,574

(22) Filed: Sep. 1, 2006

(65) Prior Publication Data

US 2007/0049656 A1   Mar. 1, 2007

Related U.S. Application Data

(60) Provisional application No. 60/713,249, filed on Sep. 1, 2005, provisional application No. 60/765,272, filed on Feb. 3, 2006.

(51) Int. Cl.
| | |
|---|---|
| *A61K 6/083* | (2006.01) |
| *A61K 6/08* | (2006.01) |
| *A61C 5/00* | (2006.01) |
| *C08F 118/02* | (2006.01) |
| *C08F 22/26* | (2006.01) |
| *C08F 299/04* | (2006.01) |
| *C08L 67/06* | (2006.01) |

(52) U.S. Cl. ............... 523/116; 523/118; 433/226; 433/228.1; 106/35; 526/319; 526/321; 525/168; 522/104; 522/107

(58) Field of Classification Search .......... 523/113, 523/115, 116, 117, 118; 433/226, 228.1; 106/35; 522/104, 107; 525/168; 526/319, 526/321

See application file for complete search history.

(56) References Cited

U.S. PATENT DOCUMENTS

| | | | |
|---|---|---|---|
| 3,991,008 A | 11/1976 | Temin et al. | |
| 4,683,287 A * | 7/1987 | Koleske et al. | 528/357 |
| 5,154,613 A * | 10/1992 | Cohen | 433/228.1 |
| 5,276,068 A | 1/1994 | Waknine | |
| 5,444,104 A | 8/1995 | Waknine | |
| 5,502,087 A * | 3/1996 | Tateosian et al. | 523/115 |
| 6,013,694 A | 1/2000 | Jia et al. | |
| 6,030,220 A | 2/2000 | Karmaker et al. | |
| 6,039,569 A | 3/2000 | Prasad et al. | |
| 6,132,215 A | 10/2000 | Prasad et al. | |
| 6,186,790 B1 | 2/2001 | Karmaker et al. | |
| 6,200,136 B1 | 3/2001 | Prasad et al. | |
| 6,270,562 B1 | 8/2001 | Jia | |
| 6,362,250 B1 | 3/2002 | Karmaker et al. | |
| 6,381,989 B1 | 5/2002 | Karmaker et al. | |
| 6,399,037 B1 | 6/2002 | Pflug et al. | |
| 6,403,676 B1 | 6/2002 | Jia et al. | |
| 6,455,608 B1 | 9/2002 | Jia et al. | |
| 6,730,156 B1 | 5/2004 | Windisch et al. | |
| 6,872,076 B2 | 3/2005 | Karmaker et al. | |
| 6,890,968 B2 | 5/2005 | Angeletakis et al. | |
| 6,899,948 B2 | 5/2005 | Zhang et al. | |

(Continued)

*Primary Examiner*—Harold Y Pyon
*Assistant Examiner*—Michael Pepitone
(74) *Attorney, Agent, or Firm*—Cantor Colburn LLP (57) ABSTRACT

A curable restorative composition is disclosed, comprising a polymerizable mono(meth)acrylate resin having a vapor pressure of 1 mm Hg or less at 20° C., a plasticizer; and a curing system for the mono(meth)acrylate resin. The composition is particularly useful for making temporary restorations. Methods of used and kits comprising the composition are also disclosed.

35 Claims, 2 Drawing Sheets

U.S. PATENT DOCUMENTS

| | | | |
|---|---|---|---|
| 2002/0045678 A1* | 4/2002 | Lopez et al. | 523/116 |
| 2002/0120033 A1* | 8/2002 | Jia et al. | 523/115 |
| 2003/0124483 A1* | 7/2003 | Jia et al. | 433/81 |
| 2003/0134933 A1 | 7/2003 | Jin et al. | |
| 2004/0249015 A1 | 12/2004 | Jia et al. | |
| 2005/0113480 A1 | 5/2005 | Usuki et al. | |
| 2005/0192374 A1 | 9/2005 | Jia et al. | |

* cited by examiner

DENTAL RESIN COMPOSITION, METHOD OF MANUFACTURE, AND METHOD OF USE THEREOF

CROSS-REFERENCE TO RELATED APPLICATIONS

This application claims the benefit of U.S. Provisional Application No. 60/713,249, filed Sep. 1, 2005, and U.S. Provisional Application No. 60/765,272, filed Feb. 3, 2006, the contents of both applications being incorporated by reference herein in their entirety.

BACKGROUND

This invention relates to dental resin compositions comprising polymerizable (meth)acrylate resins, their method of manufacture, and the use of such resins for restorative dentistry.

In recent years, materials used for dental restorations have principally comprised acrylate or methacrylate ("(meth)acrylate") resins. Resins commonly used in most dental applications are multi-functional (meth)acrylates in combination with filler(s), which gives proper polymerization cross-linking and strength to satisfy the needs of a tooth restoration. An especially important multifunctional methacrylate resin is the condensation product of bisphenol A and glycidyl methacrylate, 2,2'-bis [4-(3-methacryloxy-2-hydroxypropoxy)-phenyl]-propane ("Bis-GMA"). Alternatively, Bis-GMA can be synthesized from the diglycidyl ether of bisphenol A and methacrylic acid. Especially when used as cements, these viscous resins are commonly used with multifunctional diluents such as tri(ethylene glycol) dimethacrylate ("TEGDMA") and hexanediol dimethacrylate ("HDDMA") to allow ready incorporation of filler(s) and enhance crosslinking and other functional properties of the compositions.

Dental compositions based on these resin materials have generally been formulated for hardness and strength, in order to provide a long-term tooth restoration. Conventional resin-based dental restorative materials, including those formed from di- and multifunctional (meth)acrylate cements, usually possess high compressive strengths (about 100 to about 450 Mpa) depending on the specific resin composition, filler type and amount, and the composition' intended used. However, in certain procedures temporary materials, that is, materials that are intended to be removed within a relatively short time period (e.g., one day to six months) are required. Such temporary materials do not require the hardness or strength of conventional compositions. Dental cements for use with temporary materials in particular do not need to be strong, and in fact, should be formulated for relatively easy removal. Accordingly, current temporary dental cements are acid-based materials such as zinc oxide-eugenol, zinc oxide-benzoic acid, calcium hydroxide-salicylic acid or its derivatives, and the like. These materials are weaker than permanent materials, and can serve the purposes of temporary cementation. However, they are also often brittle and, upon removal or breakage, leave unwanted residue on tooth surfaces.

Prosthodontic dental materials such as denture bases and denture base liners have also been manufactured using (meth)acrylate resins, particularly methyl methacrylate (MMA), methyl methacrylate polymers, ethyl methacrylate (EMA), and butyl methacrylate, in combination with a plasticizer. However, use of these methacrylates for dental restorative materials chairside is limited based on their odor. Methyl methacrylate monomer, for example, has a vapor pressure of 29 millimeter (mm) of mercury (Hg) at 20° C., EMA has a vapor pressure of 15 mm Hg at 20° C., and butyl methacrylate has a vapor pressure of 2 mm Hg at 20° C. The strong smell of these materials renders them unsuitable for placement directly in a patient's mouth and undesirable to work with in a dental laboratory.

There accordingly remains a need in the art for dental restorative materials, particularly cements, useful for temporary dental restorations. There particularly remains a need for materials that are not brittle and/or that can be cleanly removed from a tooth surface. There further remains a need for materials that can be used for laboratory manufacture of temporary restorations. It would further be advantageous for the materials to be free of objectionable odors at room temperature, and even more advantageous to package these materials in a convenient form, such as a kit or tray.

SUMMARY

A curable dental restorative composition useful for the formation of a temporary dental restoration comprises a mono(meth)acrylate resin having a vapor pressure of 1 mm Hg or less at 20° C., a plasticizer, and a curing system for the mono(meth)acrylate resin. In one embodiment, the curable dental restorative composition further comprises a (meth)acrylate comprising an acidic moiety. Other optional components can also be present, for example a filler, a stabilizer, a colorant, and the like. Such compositions have a compressive strength of about 0 to about 50 MPa, measured per ANSI/ADA Specification No. 66.

In another embodiment, the above-described composition is part of a kit.

A method for the formation of a temporary dental restoration for placement at a site to be restored comprises applying the above-described curable composition to at least a portion of the temporary dental restoration, curing the curable composition, and placing the temporary dental restoration at the site to be restored.

In another embodiment, a method of temporarily restoring a site on a tooth comprises preparing a site on the tooth for restoration; applying to at least a portion of the site the above-described curable composition, and curing the curable composition.

Also disclosed herein are methods for making a laboratory dental restoration. The method comprises forming a first impression of a tooth, preparing the tooth, forming a model of the prepared tooth, and forming a restoration from the first impression and the model, wherein the restoration comprises a curable restorative composition comprising a polymerizable mono(meth)acrylate resin having a vapor pressure of 1 mm Hg or less at 20° C.

A method of making a dental restoration comprises forming a first impression of a tooth, preparing the tooth, forming a second impression of the prepared tooth, forming a model of the prepared tooth in the second impression, forming a restoration from the first impression and the model, wherein the restoration comprises a curable restorative composition comprising a polymerizable mono(meth)acrylate resin having a vapor pressure of 1 mm Hg or less at 20° C.

A method of making a dental restoration comprises forming a first impression of a tooth, preparing the tooth, forming a second impression of the prepared tooth, forming a model of the prepared tooth in the second impression, disposing a curable restorative composition comprising a polymerizable mono(meth)acrylate resin having a vapor pressure of 1 mm Hg or less at 20° C. into the first impression, forming an impression into the curable restorative composition with the model, and curing the curable restorative composition to form a restoration.

BRIEF DESCRIPTION OF THE DRAWINGS

The following figures are exemplary embodiments, wherein like elements are numbered alike.

DETAILED DESCRIPTION OF PREFERRED EMBODIMENTS

The present disclosure is directed to curable dental restorative compositions useful for the formation of a temporary dental restoration. The compositions are suitable for either chairside or laboratory use. In one embodiment, the composition is a cement that is prepared using a combination of a curable mono(meth)acrylate resin having a vapor pressure of 1 mm Hg or less at 20° C., a non-reactive plasticizer, and a cure system. As used herein, a "dental restorative" composition and a "dental restorative" material excludes materials used in prosthodontics (e.g., denture bases), and refers to compositions for the direct restoration of teeth, for example filling a tooth cavity, lining a tooth cavity, forming a jacket crown of a tooth, and the like, as well as in endodontic procedures.

Further as used herein, a "mono(meth)acrylate resin" is a monomeric, oligomeric, or polymeric material containing one (meth)acrylate functional group per molecule. Such resins are capable of limited cross-linking through the ethylenic unsaturation of the (meth)acrylate group, but are not expected to crosslink to the degree found in conventional multifunctional (meth)acrylate resins. Appropriate selection of the type and amount of mono(meth)acrylate resin allows adjustment of the compressive strength, removal characteristics, and other properties of the restorative material. Use of a non-reactive plasticizer is also hypothesized to allow adjustment of these properties.

In one embodiment, the curable restorative compositions are used as cements in the preparation of temporary dental restorations, as their reduced compressive strength facilitates removal of the restoration without damage to a tooth and without leaving unwanted residue to interfere with its replacement with a more permanent material. Although these curable restorative cement compositions are referred to herein as "cements", it is to be understood that they are also of use where high strength is not required, such as in endodontic therapy (e.g., root canal filling, sealing, or cementation), a temporary cementation media for a trial fitting of a permanent dental restoration of crown or bridge, or other applications of a temporary nature.

It has been found by the inventors hereof that an improved temporary cement restorative composition, and one that is suitable for the formation of chairside or laboratory dental restorations, is obtained using a mono(meth)acrylate resin that has a vapor pressure of 1 mm Hg or less at 20° C. In one embodiment, the mono(meth)acrylate resin has a vapor pressure of about 0.5 mm Hg or less at 20° C., and in another embodiment the mono(meth)acrylate resin has a vapor pressure of about 0.05 mm Hg or less at 2° C. In still another embodiment, the mono(meth) resin has a vapor pressure of about 0.01 mm Hg or less at 25° C. Thus, "mono(meth) acrylate resins" as used herein excludes unfunctionalized $C_1$-$C_4$ alkyl esters of mono(meth)acrylates such as methyl (meth)acrylate), ethyl(meth)acrylate, butyl(meth)acrylate, and the like. In one embodiment, such unfunctionalized $C_1$-$C_4$ alkyl esters of (meth)acrylates are also excluded from the compositions described herein. Such resins are of particular utility in temporary cement formulations.

A wide variety of mono(meth)acrylate resins that satisfy the above vapor pressures can be used, including mixtures of mono(meth)acrylate resins. The resins will generally be of higher molecular weight, and can be functionalized, for example with hydroxy, amino, carboxylic acid, sulfonic, phosphoric, phosphonic, and the like groups.

For example, suitable types of mono(meth)acrylate resins includes $C_5$-$C_{32}$ alkyl(meth)acrylates, and hydroxy-terminated alkyl(meth)acrylates such as 2-hydroxyethyl methacrylate (HEMA), 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol monomethacrylate, pentaethyleneglycol monoacrylate, dipropyleneglycol monomethacrylate, dipropyleneglycol monoacrylate, hydroxy polyethyl methacrylates, phenoxyhydroxyphenyl methacrylate and the like.

Another suitable class of mono(meth)acrylates are those derived by the reaction of a hydroxyl-functional mono(meth) acrylate with a monomer containing a carboxylic acid, lactone, ester, acyl halide, or other group reactive with the hydroxyl group. Suitable hydroxyl-functional mono(meth) acrylates include hydroxy ($C_1$-$C_{12}$)alkyl (meth)acrylates such as 2-hydroxyethyl(meth)acrylate) (HEMA), and those described above. HEMA is preferred.

Suitable monomer compounds with reactive groups include, for example, L-lactide, DL-lactide, glycolide, caprolactone, and the like, as well as (meth)acrylate- or vinyl-terminated siloxane resins and/or epoxy terminated mono (meth)acrylate resins.

Preferably, the mono(meth)acrylate is not methyl methacrylate (MMA) and the functional group contributed by the monomer is something other than a methoxy group, as simple MMA monomers have an undesirable odor.

The mono(meth)acrylate resin product of the reaction can be monomeric, oligomeric, or polymeric. The product resins are selected so as to provide the desired degree of reactivity and the desired properties to the restoration. One example of such a mono(meth)acrylate resin is 2-(caprolactone)ethyl methacrylate (CLMA), which is an addition product of HEMA with gamma-caprolactone, commercially and available from Aldrich Chemicals. Other suitable mono(meth) acrylate resins are described in commonly assigned U.S. Pat. No. 6,455,608 to Jia et al.

A suitable amount of the mono(meth)acrylate resin in the curable restorative composition will vary depending on the particular type of resin used, the reactivity of the resin, the degree of crosslinking desired, the desired properties of the cured composition, and like considerations. In various embodiments, the curable dental restorative composition comprises about 10 to about 90 weight percent (wt. %) mono (meth)acrylate resin, based on the total weight of the composition, optionally about 20 to about 80 wt. %, more specifically about 30 to about 70 wt. %.

Curable temporary dental cement restorative composition further comprise a plasticizer that is compatible with the uncured mono(meth)acrylate resin, in particular, that is miscible with the uncured mono(meth)acrylate resin. The plasticizer is preferably non-reactive with the other components in the composition. Suitable plasticizers are selected so as to decrease the compressive strength of the cured resin, increase the elasticity and/or resiliency of the cured composition, make the composition softer upon curing and/or enhance clean removal of the temporary restorative material.

Suitable plasticizers are nontoxic in the oral environment and include, for example, hydrocarbon oils, silicone oils, glycerin, glycerides (esters of fatty acids with glycerol), polyethylene oxide, other water soluble/expandable polymers such as polyvinyl alcohol, xathan gum, cellulose, phthalate resins such as dibutyl phthalate, diethyl phthalate, and dioctyl phthalate, polyalkylene glycols including polyethylene glycols, polyoxyethylene glycols, halogenated hydrocarbon waxes, hydrogenated waxes and wax esters from the reaction of fatty alcohols and acids, and the like, as well as combinations comprising at least one of the foregoing. Polyethylene glycols (PEGs) are especially suitable, for example polyethylene glycols having two, three or more ethylene glycol units are suitable, optionally polyethylene glycols having from 2 to about 200 ethylene glycol units or more are most suitable.

The curable dental cement composition comprises about 5 to about 80 wt. % plasticizer, based on the total weight of the composition, optionally about 10 to about 70 wt. %, more specifically about 20 to about 60 wt. % of the composition.

In addition to the mono(meth)acrylate, plasticizer, and cure system, the restorative compositions can comprise other components to adjust the handling and/or final properties of the composition. For example, viscous resins, multifunctional resins, and/or diluents (each of which is described in further detail below) can be added in amounts of 0 to about 50 wt. % of the total weight of the curable components, optionally about 0.5 to about 20 wt. %, for example, about 1 to about 10 wt. %. Such resins can provide a limited amount of crosslinking to adjust the final properties of the composition. Each of these additional curable components has a vapor pressure of less than or equal to about 1 mm Hg at 20° C., preferably less than or equal to about 0.5 mm Hg, more preferably less than or equal to about 0.1, still more preferably less than or equal to about 0.5 mm Hg, even more preferably less than or equal to about 0.01 mm Hg at 20° C. In one embodiment the resin component of the dental restorative composition consists of (meth)acrylates having a vapor pressure of 1.0 or less, specifically 0.5 or less, more specifically 0.1 or less, still more specifically 0.01 or less mm Hg at 20° C.

Exemplary viscous resins, which are used in limited amounts in dental cements, include Bis-GMA, urethane dimethacrylate ("UDMA"), polyurethane dimethacrylate ("PUDMA"), the polycarbonate dimethacrylates (PCDMA) disclosed in U.S. Pat. Nos. 5,276,068 and 5,444,104 to Waknine, which is the condensation product of two parts of a hydroxyalkylmethacrylate and 1 part of a bis(chloroformate), the ethoxylated bisphenol A dimethacrylates (EBPDMA) as disclosed in U.S. Pat. No. 6,013,694 to Jia, et al. and the like, in amounts of 0 to about 50 wt. % of the total weight of the curable components. EBPDMA in particular is effective in reducing the water sorption of the final product. A combination of the aforementioned resins can also be used.

Low viscosity multifunctional (meth)acrylate diluent monomers can be present in the compositions. Such monomers provide additional crosslinking and allow the viscosity of the composition to be adjusted for easy delivery via cannula, while maintaining advantageous physical properties of the polymerized product. Exemplary diluent monomers include but are not limited to liquid dimethacrylate, trimethacrylate, or higher monomers, such as glycerol dimethacrylate, ethylene glycol dimethacrylate, tri(ethylene glycol) dimethacrylate (TEGDMA), tetra(methylene glycol) dimethacrylate, trimethylolpropane trimethacrylate, 1,6-hexanediol dimethacrylate (HDDMA), and 1,3-butanediol dimethacrylate. These monomers are characterized by relatively low molecular weight (e.g., 400 or less) and low viscosity. Multifunctional diluent monomers can be used in amounts of 0 to about 50 wt. % of the total weight of the curable components, preferably about 0.5 to about 20 wt. %, more preferably about 1 to about 10 wt. %.

Another component is an acid-containing compound, examples of which include, but are not limited to, maleic acid, itaconic acid, methacrylic acid, acrylic acid, tartaric acid, ethylenediaminetetraacetic acid (EDTA), EDTA salt, citric acid, a homopolymer or copolymer of an alpha, beta-unsaturated carboxylic acid such as poly(acrylic acid), a copolymer of acrylic acid such as poly(acrylic acid-maleic acid) copolymer, poly(acrylic acid-itaconic acid) copolymer, or poly(acrylic acid-maleic acid-itaconic acid) copolymer, a polymerizable homopolymer or copolymer of an alpha, beta-unsaturated carboxylic acid such as (meth)acrylated poly (acrylic acid), a (meth)acrylated poly(acrylic acid) copolymer such as a (meth)acrylated poly(acrylic acid-maleic acid) copolymer or (meth)acrylated poly(acrylic acid-maleic acid-itaconic acid) copolymer, maleic anhydride, trimellitic anhydride, 4-META (4-methacryloxyethyltrimellitic anhydride), an addition product of a mono- or dianhydride compound with a hydroxyalkylmethacrylate compound such as PM-HEMA (the addition product of pyromellitic acid anhydride and 2-hydroxyethyl methacrylate), PM-GDM (the addition product of pyromellitic acid anhydride and glycerol dimethacrylate), BTDA-HEMA (the addition product of 3,3', 4,4'-benzophenone tetracarboxylic dianhydride and hydroxyethyl methacrylate), and PA-HEMA (the addition product of phthalic anhydride and hydroxyethyl methacrylate), MA-GDM (the addition product of maleic anhydride and glycerol dimethacrylate), an alkyl sulfonic acid, an aromatic sulfonic acid, an alkyl sulfinic acid, an aromatic sulfinic acid, a monoalkyl phosphate, a dialkyl phosphate, an aryl alkyl phosphate, an aryl phosphate, phenyl methacryloxyethyl phosphate), glyceryldimethacrylate phosphate, pentaerythritol triacrylate phosphate, methacryloyloxydecyl phosphate, hydroxyethylmethacrylate phosphate, and bis(hydroxyethylmethacrylate) phosphate, or a combination comprising at least one of the foregoing acid-containing compounds.

In specific embodiments, an acid-containing compound has at least one acidic group and at least one ethylenically unsaturated moiety selected from the group consisting of an acrylate, a methacrylate, and a vinyl group, so that it can copolymerize with other monomers. Examples of acidic compounds having at least one acidic group and at least one ethylenically unsaturated moiety include, but are not limited to, methacrylated poly(acrylic acid), methacrylated poly (acrylic acid) copolymer such as methacrylated poly(acrylic acid-maleic acid) copolymer and methacrylated poly(acrylic acid-maleic acid-itaconic acid) copolymer, 4-META, PM-GDM, PM-HEMA, BTDA-HEMA, PA-HEMA, MA-GDM, phenyl methacryloxyethyl phosphate, glyceryldimethacrylate phosphate, pentaerythritol triacrylate phosphate, methacryloyloxydecyl phosphate, hydroxyethylmethacrylate phosphate, and bis(hydroxyethylmethacrylate) phosphate. In other embodiments, acidic compounds are those having at least one phosphate group and at least one ethylenically unsaturated moiety selected from the group consisting of an acrylate, a methacrylate, and a vinyl group, so that it can copolymerize with other monomers, for example phenyl methacryloxyethyl phosphate, glyceryldimethacrylate phosphate, pentaerythritol triacrylate phosphate, methacryloyloxydecyl phosphate, hydroxyethylmethacrylate phosphate, and bis(hydroxyethylmethacrylate) phosphate.

In one embodiment, multifunctional (meth)acrylate resins having additional functional groups, for example acidic groups are used in the curable temporary dental restorative compositions. In a particular embodiment, the curable dental cement composition comprises a multifunctional (meth)acrylate that comprises an acid moiety. Suitable acid moieties include carboxylic acid groups, phosphoric acid groups, sulfonic acid groups, and the like. These resins can be used to enhance the adhesive properties of the curable dental restorative composition. Useful resins of this type include, for example, the (meth)acrylate esters of acids such as benzene tetracarboxylic acid (BTA), preferably benzene-1,2,4,5-tetracarboxylic acid, pyromellitic acid (PMA), 1,3dihydro-1,3-dioxoisobenzofuran-4,5-dicarboxylic acid, 1,3-dihydro-1,3-dioxoisobenzofuran-5,6-dicarboxylic acid, trimellitic acid, terephthalic acid, phthalic acid, benzoic acid, 4'-(4,4'-isopropylidenediphenoxy)-bis(phthalic acid) (IBA), and the like. A specific type of multifunctional (meth)acrylate resin is described in U.S. patent application Ser. No. 11/046,093, filed Jan. 28, 2005, and includes those of formula (I):

wherein n is 0, 1, 2, or 3, q is 0 or 1, A is an anhydride group, and a is 0 or 1. As is known, the anhydride group (—C(O)—O—C(O)—) is linked via its two carbon atoms to two ortho carbons of the phenyl ring. Preferably, a is 0. In another embodiment, a is 0 and n is preferably 1 or 2.

Further in structure (I), $R^1$, $R^2$, $R^3$, and $R^4$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene), wherein x and y are each independently an integer from 1 to 10. In one embodiment, $R^1$, $R^2$, $R^3$, and $R^4$ are each independently hydrogen, hydroxy, or $C_1$-$C_{12}$ alkyl, and x and y is each independently an integer from 1 to 6. More preferably $R^1$, $R^2$, $R^3$, and $R^4$ are each independently hydrogen or $C_1$-$C_6$ alkyl.

$R^5$ in structure (I) is a hydrogen or methyl group, and is preferably a methyl group.

M in structure (I) is a carbonyl-containing group, in particular wherein G and J are each independently oxygen or $NR^6$, wherein $R^6$ is hydrogen or $C_1$-$C_6$ alkyl; and m is 1, 2, 3, or 4. Preferably, M is wherein G is oxygen, and m is 1, 2, or 3. When a is 1, n+m+q is 1, 2, 3, or 4, and when a is 0, n+m+q is 1, 2, 3, 4, 5, or 6.

W in structure (I) is a hydrocarbyl linking group having a valency corresponding to z, the number of (meth)acrylate groups, plus one. W can be aromatic or aliphatic. Suitable aromatic groups are phenyl and naphthyl, and suitable aliphatic groups are $C_1$-$C_{12}$ alkyl, cycloalkyl, alkenyl, or alkynyl groups. In one embodiment, the improved dental resin composition comprises a polymerizable (meth)acrylate of the general structure (I) wherein W is —$(CR^6R^7)_w$— and z is one, wherein $R^6$ and $R^7$ are each independently hydrogen, hydroxy, $C_1$-$C_{12}$ alkyl, $C_1$-$C_{12}$ perhaloalkyl, $C_1$-$C_{12}$ alkoxy, $C_1$-$C_{12}$ perhaloalkoxy, $C_2$-$C_{12}$ alkenyl, $C_2$-$C_{12}$ alkynyl, ($C_1$-$C_6$ alkyl)-O—($C_1$-$C_6$ alkylene), or hydroxy($C_1$-$C_6$ alkylene), wherein w is an integer of 1 to 5, preferably 1 to 3.

In a specific embodiment, $R^1$, $R^2$, $R^3$, $R^4$, $R^6$, and $R^7$ are each independently hydrogen, hydroxy, or $C_1$-$C_{12}$ alkyl, and x and y is each independently an integer from 1 to 6. More preferably $R^1$, $R^2$, $R^3$, $R^4$, $R^6$, and $R^7$ is each independently hydrogen or $C_1$-$C_6$ alkyl. An exemplary resin of this type is derived from the reaction of one mole of benzenetetracarboxylic acid dianhydride (BTAD) or pyromellitic dianhydride (PMDA), with two moles of a hydroxy-containing (meth)acrylate, for example caprolactone 2-(methacryloyloxy)ethyl ester (CLMA, or 2-(6-hydroxy-1-oxo-hexyloxy) ethyl methacrylate), at elevated temperature in the presence of a catalyst, for example stannous ethylhexanoate (SEH). The resulting reaction product (BTA-CLMA or PMDA-CLMA, respectively) contains two (meth)acrylate groups and two carboxylic acid groups. Any number of the remaining carboxylic acid groups can further be reacted with an additional hydroxy-containing (meth)acrylate monomer to form a modified polymerizable (meth)acrylate. The ratio of moles of hydroxy-containing (meth)acrylate monomer to moles of anhydride or carboxylic acid, as well as the reaction conditions and/or starting materials, can be varied to provide a wide range of polymerizable (meth)acrylate products. The ratio of moles of hydroxy-containing (meth) acrylate monomer to moles of aromatic anhydride and/or carboxylic acid can be about 0.1 to about 5, preferably about 0.5 to about 4, more preferably about 0.75 to about 3, and yet more preferably about 1 to about 2.

The above-described hydroxy-functional (meth)acrylates can also be used as diluent monomers.

The curable dental compositions further include a cure system. Suitable curing systems for use with acrylate or methacrylate-containing compounds are known in the art, and can be a light-cure, a heat-cure, or a self-cure system, or a combination thereof. Use of a dual-cure system (light and self-cure) and optional accelerators yields a composition that cures evenly and completely.

The light-cure system comprises a light-activated polymerization initiator, including but not limited to photoinitiators such as benzil, benzoin, benzoin methyl ether, DL-camphorquinone (CQ), phosphine oxide, and benzil diketones. Either UV-activated cure or visible light-activated cure (approx. 230 to 750 nm) is acceptable. The amount of photoinitiator is selected according to the curing rate desired. A minimally catalytically effective amount is generally about 0.01% by weight of the curable components of the composition, and will lead to a slower cure. Faster rates of cure are achieved with amounts of greater than about 0.01% to about 5% by weight of the curable components. Cure accelerators can be used in the light-cure systems, for example tertiary amines such as ethyl 4-dimethylaminobenzoate ("EDMAB") and tertiary amino acrylates such as 2-(diethylamino)ethyl methacrylate ("DEAEMA"), in amounts of about 0.05 to about 0.5 percent by weight of the curable components.

A heat-cure system comprises a heat-activated initiator such as benzoyl peroxide, lauroyl peroxide, dicumyl peroxide, 1,1'-azobis(cyclohexanecarbonitrile), or other free radical initiators. The amount of initiator is selected according to the curing rate desired. A minimally catalytically effective amount is generally about 0.5% by weight of the curable components, and will lead to a slower cure. Faster cure is achieved with above about 0.5% to about 6.0% by weight of the curable component. Light-cure, heat-cure, and dual light-/heat-cure systems are advantageous because the curable restorative composition can be supplied to the practitioner pre-mixed, that is, as a single-component mixture ready for application to the site of restoration. In a particularly preferred embodiment, the composition is supplied in pre-packaged syringes, compules, or cartridges.

Optionally, the cure system can comprise a self-cure system. These are generally formulated two parts with the other components of the restorative material, stored separately, and mixed prior to use to initiate cure. Suitable self-cure systems comprise an initiator such as a peroxide in one part, and an accelerator such as a tertiary amine, generally tertiary aromatic amine such as ethyl 4-(dimethylamino)benzoate ("EDMAB"), 2-[4-(dimethylamino)phenyl]ethanol, N,N-dimethyl-p-toluidine (DMPT), bis(hydroxyethyl)-p-toluidine, and triethanolamine in a second part. Such accelerators are generally present in amounts of about 0.5 to about 4.0% by weight of the polymeric component. Another self-curing system comprises thiourea or thiourea derivatives as the reductant and hydrogen peroxide as the oxidant, as described in U.S. Pat. No. 3,991,008. Optionally, a self-cure system can be combined with a light-cure system.

Fillers that can be used in the curable restorative compositions include organic and inorganic particulates and fibrous fillers known in the art, such as particulate poly(lactide), poly(glycolide), poly(lactide-co-glycolide) or poly(methacrylate), or particulate or fibrous silica, silicate glass, quartz, barium silicate, strontium silicate, barium borosilicate, strontium borosilicate, borosilicate, lithium silicate, lithium aluminum silicate, amorphous silica, glass fibers, alumina, zirconia, tin oxide, and titania. Fibrous fillers such as those disclosed in U.S. Pat. Nos. 6,013,694, 6,403,676 and 6,270,562 to Jia and Jia et al. can be used. Radiopaque/high refractive index materials, such as apatites, can be optionally included in the filler compositions. Suitable high refractive index filler materials include, but are not limited to, high refractive index silica glass fillers, and inert, non-toxic radiopaque materials such as barium sulfate, bismuth subcarbonate, bismuth oxide ($Bi_2O_3$), bismuth oxychloride, and zirconium oxide, in micro- or nanoscaled sizes. The relative amounts of radiopaque/high refractive index materials are readily determined by those of ordinary skill in the art, depending on the particular fillers used, the intended application, the desired final properties (e.g., hardness and radiopacity), and the like.

Suitable fillers have particle sizes of about 0.01 to about 5.0 micrometers, and can further comprise bound or unbound silicate colloids of about 0.001 to about 0.2 micrometers. The fillers can also be treated with a silane-coupling agent to increase adhesion with the polymerizable resin. Commercially available silane treated fumed silica based on Aerosil A200 can be obtained from Degussa Corp under the names of Aerosil R711 and R7200, and non-silane treated amorphous silica such as Aerosil® OX-50 from Degussa.

The amount of total filler in the dental restorative material can vary from about 1 to about 90 weight percent, based on the total weight of the dental restorative material. The amount used is determined by the requirements of the particular application. The composition can be used, for example, for making temporary crowns and bridges, as a luting cement, as a root canal sealant, a root canal filling material, a cement for use in a root canal, an adhesive, as a tooth filling material, implant material, bone cement and pulp capping composition. Crown and bridge materials generally comprise about 60 to about 90 weight percent filler; luting cements comprise about 20 to about 80 weight percent filler; root canal sealants generally comprise about 30 to about 70 weight percent filler; adhesives generally comprise about 0 to about 30 weight percent filler; and tooth filling restorative materials comprise about 50 to about 90 weight percent filler, and so on, with the remainder in all cases being the polymerizable (meth)acrylate and other optionally added resins.

The compositions can further comprise other additives, for example pigments; anti-oxidants, for example BHT (2,6-di-tert-butyl-4-methylphenol) or hydroquinone methyl ether in amounts in the range from about 0.1 to about 0.3% by weight of the polymerizable components; ultraviolet stabilizers to prevent discoloration, for example benzophenones such as 2-hydroxy-4-methoxybenzophenone, benzotriazoles, such as 2-(2'-hydroxy-5'-methylphenyl)benzotriazole, 2-(2-hydroxy-5-tert-octylphenyl)benzotriazole (available under the trade name UV-54 from American Cyanamid Company) and other derivatives thereof; fluorescent whitening agents such as 2,5-bis(5-tert-butyl-2-benzoxazole) thiophene (available under the trade name UV-OB); trace amounts of FDA and FDC approved dyes, for example iron oxides, yellow No. 5, yellow No. 6, and the like; and other additives known in the art.

Medicaments can also be included in the compositions in a therapeutically effective amount, for example to relieve pain, prevent infection, prevent inflammation, alleviate sensitivity, and the like. Such amounts are generally about 0.001% to about 10% by weight of the total composition, more commonly about 0.001 to about 2 wt. % of the total composition. Suitable medicaments include but are not limited to pain relieving agents such as Novocaine (procaine hydrochloride), Benzocain (ethyl aminobenzoate), ascorbic acid, butacaine sulfonate, and dibutacaine hydrochloride; antibiotics such as sulfadiazine, procaine penicillin, aureomycin, streptomycin, tetramycin, chloramphenicol, butabarbital, diethyl stilbestrol, and the like; anti-inflammation agents such as p-aminosalicylic acid, aspirin, chlorohexadine, and the like; and desensitizing agents such as sodium fluoride, potassium nitrate, and the like.

The curable dental compositions can be provided to the practitioner as a one-part composition, for example in the form of an injectable liquid or a paste. This form is highly convenient for the practitioner, as it obviates the need for any pre-mixing. The viscosity of such one-part formulations can be adjusted to allow application using a syringe fitted with a cannula, a compule, or the like. In this embodiment liquid or other low viscosity resin components are preferred, and use of high-viscosity resins (such as Bis-GMA) or solid resins is minimized or excluded.

Alternatively, the curable dental restorative compositions can be provided to the practitioner as a two-part system, wherein the first part can comprise the polymerizable mono (meth)acrylate, filler, and one part of the self-cure system, e.g., a peroxide. The second part can comprise the second part of the self-cure system and optional diluent monomers. In one advantageous embodiment, each of the parts is formulated as a paste, which facilitates mixing. In this embodiment the resin composition if formulated using liquid or other low viscosity resins, and high viscosity or solid resins are minimized or eliminated. When needed, the two parts are metered out and then mixed using a spatula or mixed through a double barrel cartridge device. The dental restorative material thus obtained is then placed on restoration or the tooth to be restored after the tooth is appropriately prepared.

A cured temporary cement composition as described herein can have a compression strength of less than or equal to about 50 MPa, optionally less than or equal to about 30 MPa or, in some embodiments, less than or equal to about 10 Mpa, measured per ISO Specification 7489-1986. The compressive strength can also be greater than or equal to about 1 Pa. Unlike compositions used in prosthodontics for the formation of dental liners, denture bases, and the like, the curable cement compositions can be formulated to be adhesive to dentition. In one embodiment, the cured compositions have good adhesion to dentition, but are also rubbery, and are easily removable from dentition without leaving unwanted residue.

The temporary crown-and-bridge compositions preferably comprise a viscous resin, a diluent monomer, an acid-containing (meth)acrylate monomer, a filler composition, and a cure system. Exemplary formulation ranges for a two-part dual cure temporary crown and bridge dental restoration made chairside or in a laboratory are shown in Table 1 below. Amounts are in parts per hundred, by weight.

TABLE 1

| Components | Base paste | Base paste | Catalyst paste | Catalyst paste |
| --- | --- | --- | --- | --- |
| Bis-GMA | — | — | 1-50 | 5-25 |
| UDMA | — | — | 1-50 | 5-25 |
| Diluent monomer | — | — | 1-50 | 5-25 |
| Acid-containing (meth)acrylate monomer | — | — | 0.1-10 | 0.1-5 |
| EBPDMA | 25-85 | 35-75 | — | — |
| BPO | — | — | 0.1-5 | 0.1-5 |
| DMPT | 0.01-5 | 0.1-2 | — | — |
| BHT | 0.01-1 | 0.05-0.5 | 0.01-1 | 0.05-0.5 |
| EDMAB | 0.01-1 | 0.05-0.5 | — | — |
| CQ | 0.01-1 | 0.05-0.5 | — | — |
| Silane | 0.1-10 | 0.5-5 | 0.1-10 | 0.5-5 |
| Filler | 25-85 | 35-75 | 25-85 | 35-75 |

The composition is mixed just prior to use in approximately equal ratios. The gel time and setting time of the compositions can be adjusted by adjusting the amount of DMPT I the base paste.

An exemplary method of a chairside procedure for restoring a tooth comprises preparing a site on a tooth to be restored; applying the above-described curable dental restorative composition comprising a mono(meth)acrylate resin having a vapor pressure of less than 1 mm Hg at 20° C., a plasticizer, a cure system and, optionally, a filler, to the site; and curing the composition. In another embodiment, a method for the formation of a temporary dental restoration for placement at a site to be restored comprises applying the above-described curable composition to at least a portion of the temporary dental restoration, placing the temporary dental restoration at the site to be restored, and curing the curable composition before or after placement. Optionally, the restoration is intended for a relatively short service period, for example, less than a six months, less than two months, less than thirty days, or less than two weeks.

In a specific embodiment, the composition is used as a cement to secure a temporary restoration such as a crown to a site on a tooth to be restored. For example, a dentist can make a custom impression tray of the site using a clear impression material. When the impression material cures, the dentist removes the impression from the site, and prepares the site to be treated. The dentist prepares the material used to form the restoration, injects the material into the impression of the site to be treated, reseats the impression back in the patient's mouth, and cures the restoration material. After the temporary restoration material cures, the impression tray and the formed temporary restoration therein is removed from the patient. The temporary restoration is obtained after trimming off the excess surrounding the bulk of the cured restorative composition and making any further adjustments that are needed to fit the restoration to the site, which can be cemented thereon using a curable cement composition as described herein.

The temporary curable restorative compositions are also useful in the production of temporary dental restorations formed via an indirect method. Such restorations are formed in a laboratory, rather than at chairside.

Figure 1:
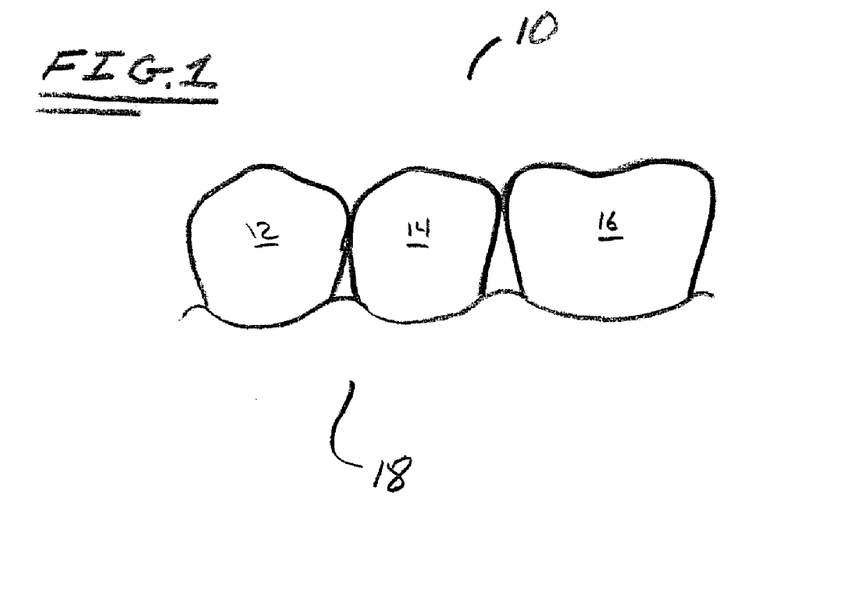
FIG. 1 is a lateral view of an exemplary mandibular arcade.

An exemplary method for production of a temporary laboratory restoration, e.g., a bridge is described generally with reference to FIGS. 1-5. FIG. 1 shows a lateral view of an exemplary mandibular arcade, generally designated 10. In the illustration the mandibular arcade comprises three teeth; a first premolar 12, a second premolar 14, and a first molar 16. Gums 18 cover the teeth. The method generally begins with forming a first dental impression of the teeth to be reconstructed. This is typically conducted chairside by the dentist performing the restoration. To form the first impression, an impression tray is filled with a dental impression material, such as a curable vinyl polysiloxane (commercially available, for example, under the name Correct-Quick® from Pentron Clinical Technologies LLC, Wallingford, Conn.). Optionally, a wax can be applied over and/or between the teeth prior to taking an impression to aid in removing the first impression. The tray is then disposed around the desired teeth, here covering the distal and proximal teeth adjacent to the tooth to be reconstructed. Once the impression material has cured, the first impression is removed from the teeth.

Figure 2:
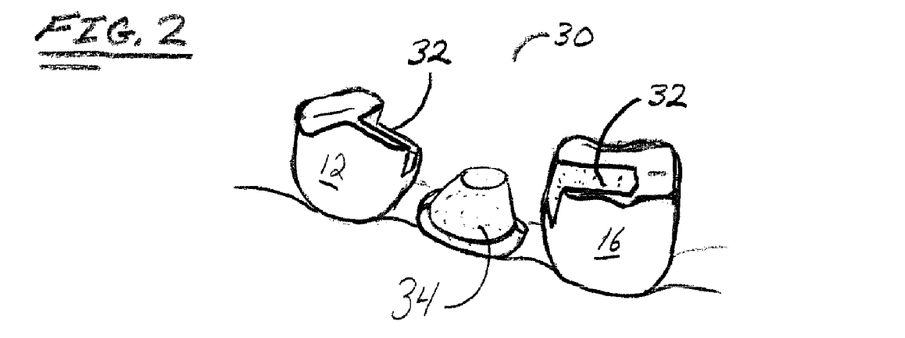
FIG. 2 is an oblique view of prepared teeth.

The teeth are then prepared for a restoration by the practitioner. For example, decay is removed from the teeth, the tooth to be reconstructed is reshaped to accept the bridge, and the distal and proximal teeth are modified so that they can structurally support the bridge. This is illustrated in FIG. 2, wherein an oblique view of the exemplary prepared teeth is generally designated 30. In the illustration, the first premolar 12, and first molar 16 have been worked with instruments (e.g., air grinding instruments) to comprise sockets 32 that can support a bridge. Also, the second premolar 14 has been worked to a stump 34, which will accept the bridge.

Once the teeth have been prepared, the practitioner takes a second impression, which will be of the prepared teeth 30. Once the second impression has be formed and given time to cure, it is removed from the prepared teeth 30. The patient can be fitted with a short-term temporary restoration, filling, coating, or so forth, as the other temporary restoration (i.e., bridge) is manufactured in a dental laboratory.

The bridge is formed in the dental laboratory using the first impression of the native teeth (i.e., first premolar 12, second premolar 14, and first molar 16), and the second impression of the prepared teeth 30 that are supplied by the dentist, and one or more of the above-described temporary dental restoration materials. In one embodiment the material(s) are provided in the form of a kit that comprises some, or all, of the compositions and instruments used to produce the restoration. Providing the material(s) in a kit form allows easy access for the user (e.g., dental laboratory professional) and convenient delivery systems.

Construction of the indirect restoration can begin with casting a model of prepared teeth utilizing the second impression. To cast the model, a casting material (e.g., gypsum, such as the Resin Rock XL5 gypsum commercially available from the WhipMix Company, Louisville, Ky.) is prepared, poured into the second impression, and allowed time to set. After the casting material sets, the second impression is removed, and the rigid model is complete. The model is a replica of the prepared teeth 30 that are illustrated in FIG. 2.

Figure 3:
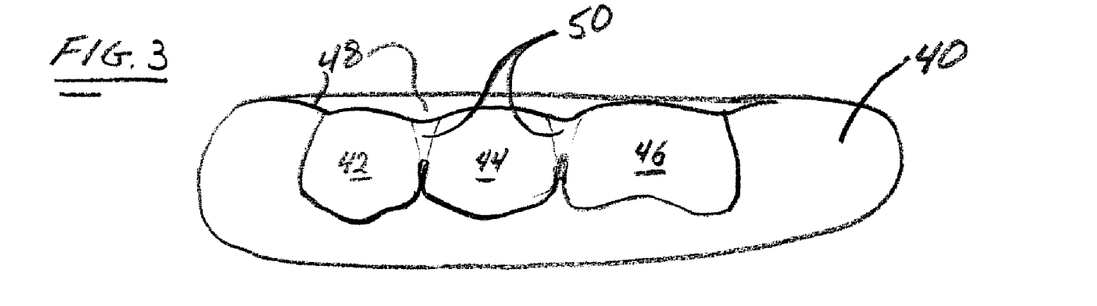
FIG. 3 is a side view of the prepared first impression.

The first impression is prepared so that the bridge can be formed therein. The first impression is prepared by removing the impression material between the impressions of teeth, which was formed by the spaces between the teeth when the impression was taken. By removing this joining material, the curable restorative composition will connect the teeth, thus forming a "bridge", as it is cast in the first impression. The joining material can be removed utilizing a scalpel, scissors, or the like. Referring now to FIG. 3, the prepared first impression is illustrated. In the illustration, the first impression 40 is illustrated in an inverted orientation, and the first impression 40 comprises a first premolar impression 42, second premolar impression 44, a first molar impression 46, as well as the gums impression 48. The first impression 40 with the impression material removed between the tooth impressions is shown as numeral 50.

Figure 4:
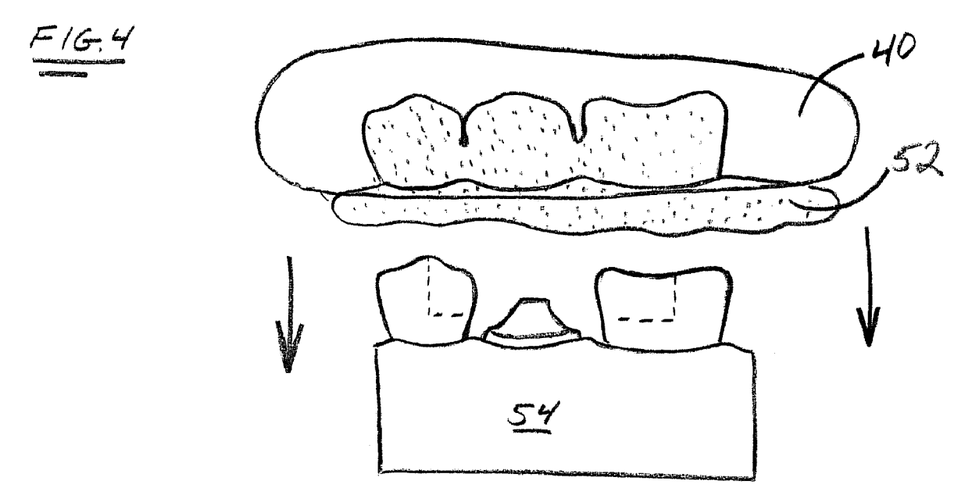
FIG. 4 is a side view of the first impression pushed onto the model.

Once the joining material 50 has been removed from the first impression 40, the bridge is cast. To cast the bridge, an amount of the curable restorative composition is then prepared and disposed into the first impression 40. While the curable restorative composition is in moldable (e.g., liquid or paste) form, the first impression 40 is pushed onto the model. This is illustrated in FIG. 4, wherein the first impression 40 is shown with the curable restorative composition 52 disposed therein, and the directional arrows indicate the direction that the first impression 40 is pushed onto the model 54. Once the first impression 40 and the model 54 have been assembled together, the curable restorative composition 52 is cured (using, e.g., self-cured, UV and/or heat). Upon cure, the first impression 40 and model 54 are disassembled and the resulting structure is the bridge.

Figure 5:
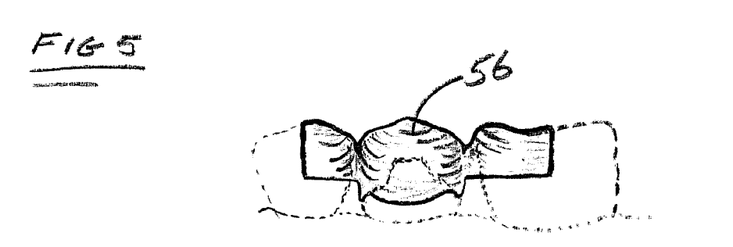
FIG. 5 is a lateral view of the bridge.

Referring now to FIG. 5, a lateral view of the bridge 56 is illustrated. When the bridge is removed from the first impression 40 and model 54, flash can be present. The flash can be removed manually using instruments (e.g., files, air grinder, scalpel). The bridge 56 is now manually shaped to better resemble native teeth and to ensure a proper fit with the model. Once the bridge 56 has been shaped as desired, it is polished. The final step can be the application of a curable glaze that is supplied in the indirect restoration kit. Once the glaze has been applied and cured, the glaze seals the bridge 56 and produces a gloss finish.

Such indirect restorations are particularly useful for "moderate-term" temporary restorations. Moderate term temporary restorations can be used for patients that anticipate additional restoration work within the expected service life of the moderate-term temporary restoration. A moderate-term restoration can also be desirable for patients that are under financial constraints, and who would like to postpone the cost of a long-term restoration.

The curable restorative composition employed to manufacture the exemplary bridge above can employ reinforcements or fillers that improve and/or modify the properties of the restoration. For example, reinforcements or fillers such as fibers, rods, wire, strips, preforms, woven and non-woven fabrics, as well as others can be employed in the indirect restoration kit for incorporation into the bridge 56. In one embodiment, reinforcing fibers can be disposed in the first impression 40 prior to adding the curable restorative composition 52. In another embodiment, fillers can be incorporated into the curable restorative composition. Other suitable reinforcements can be found in commonly assigned patents; U.S. Pat. No. 6,030,220 to Karmaker et al., U.S. Pat. No. 6,039,569 to Prasad et al., U.S. Pat. No. 6,132,215 to Prasad et al., U.S. Pat. No. 6,186,790 to Karmaker et al., U.S. Pat. No. 6,200,136 to Prasad et al., U.S. Pat. No. 6,362,250 to Karmaker et al., U.S. Pat. No. 6,381,989 to Karmaker et al., and U.S. Pat. No. 6,872,076 to Karmaker et al., which are herein incorporated by reference.

The above-described curable temporary restoration materials can be provided to the practitioner as part of a kit with other components suitable for the chairside or laboratory preparation of a dental restoration. Such materials include, for example, other types of dental adhesives, other types of dental cements, primers, dental filling materials, root canal sealants, pulp capping materials, crown and bridge materials, and the like. In a preferred embodiment, each of the foregoing materials is formulated for the production of a temporary dental restoration. The composition(s) can be packaged in one or more containers (including syringes, compules, or syringe cartridges) as a one-part or two-part formulation. In embodiments comprising a self-curing composition, the container can comprise two or more counterparts, each holding one portion of the composition to keep the portions separated from each other until they are mixed for use.

The components of the kit can be selected to provide a kit for use chairside use or laboratory use. Chairside kits can comprise, for example components for the formation of chairside dental restorations such as primers, other bonding agents, crown and bridge materials, pulp capping agents, and the like. Tools such as mixing devices, mixing pads, spatulas, and the like can also be included, as well as instructions for use. In one embodiment the kit comprising the above-described curable dental restorative material(s) further comprises other components for the formation of a chairside temporary dental restoration, for example one or more of a material for making a clear custom impression tray, a material for making a temporary restoration, and a glaze material.

Laboratory kits can comprise, for example, a moderate-term temporary crown and bridge temporary dental restoration material, a casting composition, and the like. Tools such as mixing devices, mixing containers, mixing pads, spatulas, and the like can also be included, as well as instructions for use.

The invention is further illustrated by the following non-limiting examples.

EXAMPLE 1

A self-cure dental restorative test cement composition was prepared by combining the various resin components in a mixing device as illustrated in Table 2 below.

TABLE 2

| Ingredients | Catalyst paste (Parts per hundred, by weight) | Base paste (parts per hundred, by weight) |
| --- | --- | --- |
| CLMA | 50.63 | 21.56 |
| BTACLMA | 2.66 | |
| PEG 400 (polyethylene glycol having a molecular weight of about 400) | | 32.33 |
| BPO | 1.6 | |
| DMPT | | 1.08 |
| BHT | 0.11 | |
| Coloring pigments | | 0.03 |
| NaF | 0.05 | |
| $KNO_3$ | 2.0 | |
| $Ca_3(PO_4)_2$ | 10.95 | |
| $BaSO_4$ | | 27 |
| Silane treated barium borosilicate glass | 16 | 14 |
| Amorphous silica (Aerosil ® OX-50 from Degussa) | 16 | |
| Amorphous silica (T530 Cab-o-Sil ® from Cabot Corporation) | | 4 |

To prepare a self-curing cement composition "A" in accordance with the invention, equal parts by weight of the Catalyst paste and Base paste components were mixed together for about 1 minute 40 seconds. The cement set in about 3 minutes 50 seconds at room temperature.

About one hour after the cement set, it was tested for hardness, together with a comparative commercial two-component resin cement "B" cured in accordance with the manufacturer's instructions. Since the cured composition A was rubbery, it was not feasible to use the Vicker's hardness testing method normally used for dental restorative materials, so a Shore A Durometer hardness number was determined. Hardness measurement results for the cured composition A and the cured comparative composition B are set forth in Table 3.

TABLE 3

| Material | Vicker's Hardness[1] | Shore A Hardness[2] |
| --- | --- | --- |
| A | Too soft to be measured | 85-90 |
| B | 29-32 | Out of scale (too hard to be measured in Shore A Durometer) |

[1](Clark, Model MTH, Clark Instruments)
[2]Shore Instruments, Instron, MA

Cured composition A above has a compressive strength of about 3 MPa when tested in accordance with ANSI/ADA Specification No. 66.

EXAMPLE 2

This example illustrates a procedure that can be followed to make use of a dental restorative composition as described in Example 1. A kit is provided, the kit comprising a silicone-based clear impression material (TempSpan™ Clear Impression material (Pentron Corp)), a dual-cured (light and self-cured) (meth)acrylate resin-based composite material designed for temporary restorations (TempSpan™ Temporary C&B composite (Pentron Corp)), in accordance with the present invention, and a (meth)acrylate resin-based light curable resin glaze (TempSpan™ VLC Glaze (Pentron Corp)).

The silicon-based impression material is used to make a custom impression tray of the tooth to be treated. When the clear impression material cures in the mouth, the dentist removes the impression, and prepares the tooth/teeth being treated. Then, the dentist prepares the temporary material and injects it into the clear impression tray corresponding to the treated tooth and reseats the impression back in the patient's mouth.

After the temporary material is cured in the patient's mouth, the dentist removes the clear impression tray with the formed temporary restoration from the patient, a temporary restoration is therefore has been obtained after trimming off the excess surrounding the bulk of the temporary restoration. Next, the dentist tries the temporary restoration and can make further adjustments, if needed, to fit the restoration in the patient's mouth. Once the desired fit is attained, the dentist uses the temporary cement as described herein to cement the temporary restoration in place inside the patient mouth, which will stay for a short period time (for less than a week to less than a few months). Lastly, the glaze is applied to the temporary restoration surface and light-cured.

EXAMPLE 3

An exemplary two-part dual cure temporary crown-and-bridge composition is made from a catalyst paste and a base paste that are stored separately and mixed prior to use. The catalyst paste is formed from 49 parts by weight of a catalyst resin (which contains 32 wt. % Bis-GMA, 32 wt. % UDMA, 33 w. % HDDMA, 3 wt. % Bis-HEMA phosphate, 0.2 wt. % BHT, and 2.5 wt. % BPO), 49 parts by weight of a barium borosilicate glass filler, and 2 parts by weight fumed silica. The base paste is formed from 49 parts by weight of a base resin (which contains 100 parts by weight EBP-DMA, 0.6 parts by weight DMPT, 0.2 parts by weight BHT, 0.2 parts by weight CQ, 0.4 parts by weight EDMAB, and colorant), 49 parts by weight silane-treated barium borosilicate glass filler, 1.6 parts by weight fumed silica, and 0.4 parts by weight $ZrO_2$.

In use, the two pastes are mixed in a ratio of 1:1 at room temperature, and the mixture has a gel of time of about 45 to about 90 seconds, and a setting time of about 105 to about 180 seconds. After self-curing and light curing (using, e.g., an Avente regular light cure of 30 seconds in a 3 mm mold, measuring 1 minute after light cure) a sample of the composition had a Barcol hardness of 75 on the top and 65 on the bottom. With self-curing only in a 3 mm mold, the composition had a Barcol hardness of 35 after five minutes, 50 after 190 minutes, 60 after 30 minutes, and 65 after one hour.

To prepare the restoration in accordance with the invention, equal parts by weight of the base paste and catalyst paste are mixed together and applied to the impression as described above.

All ranges directed to the same component or property disclosed herein are inclusive and independently combinable. The terms "first," "second," and the like do not denote any order, quantity, or importance, but rather are used to distinguish one element from another, and the terms "a" and "an" do not denote a limitation of quantity, but rather denote the presence of at least one of the referenced item. Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. As used herein, the term "(meth)acrylate" is intended to encompass both acrylate and methacrylate groups. The modifier "about" used in connection with a quantity is inclusive of the stated value and has the meaning dictated by the context (e.g., includes the degree of error associated with measurement of the particular quantity). All patents identified by number herein are incorporated by reference in their entirety.

While the invention has been described with reference to exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A curable temporary removable restorative cement composition comprising:
   a polymerizable mono(meth)acrylate resin having a vapor pressure of 1 mm Hg or less at 20° C., wherein the polymerizable mono(meth)acrylate resin comprises the reaction product of lactide, glycolide, caprolactone, or a mixture comprising one or more thereof, and a hydroxyl-functional mono(meth)acrylate resin;
   a plasticizer; and
   a curing system for the mono(meth)acrylate resin, wherein the composition comprises, based on the total weight of the composition, about 20 to about 90 wt.% of a polymerizable mono(meth)acrylate; about 5 to about 80 wt.% of a non reactive plasticizer; and about 0.01 to about 5 wt.% of a curing system, wherein solid resins are excluded from the composition,
   wherein the composition, upon being cured, has a compression strength of less than 50 MPa, measured per ANSI/ADA Specification No. 66.

2. The curable temporary removable restorative cement composition of claim 1, wherein the hydroxyl-functional mono(meth)acrylate resin comprises a hydroxyalkyl (meth)acrylate wherein the alkyl group has from 1 to 12 carbons.

3. The curable temporary removable restorative cement composition of claim 2, wherein the hydroxyl-functional mono(meth)acrylate resin is 2-hydroxyethyl methacrylate, 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol methacrylate, hydroxypolyethyl methacrylate, pentaethyleneglycol monoacrylate, dipropyleneglycol monomethacrylate, dipropyleneglycol monoacrylate, phenoxyhydroxyphenyl methacrylate, or a mixture comprising at least one of the foregoing.

4. The curable temporary removable restorative cement composition of claim 1, wherein the mono(meth)acrylate comprises 2-(caprolactone)ethyl methacrylate.

5. The curable temporary removable restorative cement composition of claim 1, wherein the curable mono(meth)acrylate is a liquid.

6. The curable temporary removable restorative cement composition of claim 1, further comprising a curable (meth)acrylate different from the curable mono(methacrylate) resin.

7. The curable temporary removable restorative cement composition of claim 6, wherein the different curable (meth)acrylate is a liquid.

8. The curable temporary removable restorative cement composition of claim 6, wherein the curable (meth)acrylate comprises a carboxylic, phosphonic, phosphoric, or sulfonic moiety.

9. The curable temporary removable restorative cement composition of claim 6, wherein the curable (meth)acrylate comprises a reaction product of a hydroxy-containing (meth)acrylate monomer and an aromatic compound comprising anhydride or dicarboxylic acid functionality.

10. The curable temporary removable restorative cement composition of claim 1, excluding any curable resin component having a vapor pressure of greater than or equal to 1 mm Hg at 20° C.

11. The curable temporary removable restorative cement composition of claim 1, excluding any component having a vapor pressure of greater than or equal to 10 mm Hg at 20° C.

12. The curable temporary removable restorative cement composition of claim 1, excluding any curable resin component that is a solid.

13. The curable temporary removable restorative cement composition of claim 1, wherein the plasticizer is a hydrocarbon oil, silicone oil, glycerin, glyceride, polyethylene oxide, polyvinyl alcohol, xathan gum, cellulose, a phthalate resin, a polyalkylene glycol, a halogenated hydrocarbon wax, a hydrogenated wax or wax ester from the reaction of a fatty alcohol and an acid, or a combination comprising at least one of the foregoing plasticizers.

14. The curable temporary removable restorative cement composition of claim 1, wherein the plasticizer comprises a polyethylene glycol.

15. The curable temporary removable restorative cement composition of claim 1, wherein the mono(meth)acrylate comprises 2-(caprolactone)ethyl methacrylate and the plasticizer comprises polyethylene glycol.

16. The curable temporary removable restorative cement composition of claim 1, wherein the curing system is a light-activated system, a self-curing two-part system, or a combination comprising at least one of the foregoing systems.

17. The curable temporary removable restorative cement composition of claim 16, further comprising a heat-activated curing system, wherein the heat-cure initiators are activated by the heat of reaction generated by the light-activated polymerization process.

18. A kit for the restoration of a tooth, comprising the curable temporary restorative cement composition of claim 1.

19. The kit of claim 18, wherein the kit further comprises a glaze, a crown and bridge material, a clear impression material, or a combination comprising at least one of the foregoing materials.

20. A method of restoring a tooth, comprising
    preparing a site on a tooth for restoration;
    applying to at least a portion of the site the curable temporary restorative cement composition of claim 1; and
    curing the curable composition.

21. The method of claim 20, further comprising contacting a temporary dental restoration to the curable temporary restorative cement composition prior to curing.

22. The method of claim 20, wherein the site to be restored is a tooth root.

23. A kit for the preparation of a temporary laboratory dental restoration, comprising the curable temporary restorative composition of claim 1.

24. The kit of claim 23, wherein the kit further comprises a glaze, a cement, a crown and bridge material, a clear impression material, or a combination comprising at least one of the foregoing materials.

25. A kit for the preparation of a temporary chairside dental restoration, comprising the curable temporary restorative composition of claim 1.

26. The kit of claim 25, wherein the kit further comprises a glaze, a cement, a crown and bridge material, a clear impression material, or a combination comprising at least one of the foregoing materials.

27. A curable temporary removable restorative composition comprising:
  about 30 to about 80 wt. % of a polymerizable mono(meth)acrylate resin having a vapor pressure of 1 mm Hg or less at 20° C., wherein the mono(meth)acrylate resin 2-(caprolactone)ethyl methacrylate;
  about 10 to about 60 wt. % of a non-reactive plasticizer; and
  a curing system for the mono(meth)acrylate resin;
  wherein the plasticizer is a hydrocarbon oil, silicone oil, glycerin, glyceride, polyethylene oxide, polyvinyl alcohol, xathan gum, cellulose, a phthalate resin, a polyalkylene glycol, a halogenated hydrocarbon wax, a hydrogenated wax or wax ester from the reaction of a fatty alcohol and an acid, or a combination comprising at least one of the foregoing plasticizers, and
  wherein the composition, upon being cured, has a compression strength of less than 50 MPa, measured per ANSI/ADA Specification No. 66.

28. The curable temporary removable restorative composition of claim 27, wherein the plasticizer comprises a polyethylene glycol.

29. The curable temporary removable restorative composition of claim 27, further comprising a curable (meth)acrylate comprising a reaction product of a hydroxy-containing (meth)acrylate monomer and an aromatic compound comprising anhydride or dicarboxylic acid functionality.

30. The curable temporary removable restorative composition of claim 27, wherein the composition has a compression strength of less than or equal to about 30 MPa.

31. The curable temporary removable restorative composition of claim 30, wherein the composition has a compression strength of less than or equal to about 10 MPa.

32. A curable temporary removable restorative composition comprising:
  about 20 to about 80 wt. % of a polymerizable mono(meth)acrylate resin having a vapor pressure of 1 mm Hg or less at at 20° C., wherein the mono(meth)acrylate resin 2-(caprolactone)ethyl methacrylate;
  about 10 to about 60 wt. % of a non-reactive plasticizer; and
  a curing system for the mono(meth)acrylate resin;
  a curable (meth)acrylate that is a reaction product of a hydroxy-containing (meth)acrylate monomer and an aromatic compound comprising anhydride or dicarboxylic acid functionality,
  wherein the plasticizer is a hydrocarbon oil, silicone oil, glycerin, glyceride, polyethylene oxide, polyvinyl alcohol, xathan gum, cellulose, a phthalate resin, a polyalkylene glycol, a halogenated hydrocarbon wax, a hydrogenated wax or wax ester from the reaction of a fatty alcohol and an acid, or a combination comprising at least one of the foregoing plasticizers, and
  wherein the composition, upon being cured, has a compression strength of less than about 30 MPa, measured per ANSI/ADA Specification No. 66.

33. The curable temporary removable restorative composition of claim 32, wherein the plasticizer is a hydrocarbon oil, silicone oil, glycerin, glyceride, polyethylene oxide, polyvinyl alcohol, xathan gum, cellulose, a phthalate resin, a polyalkylene glycol, a halogenated hydrocarbon wax, a hydrogenated wax or wax ester from the reaction of a fatty alcohol and an acid, or a combination comprising at least one of the foregoing plasticizers.

34. The curable temporary removable restorative composition of claim 32, wherein the plasticizer comprises a polyethylene glycol.

35. The curable temporary removable restorative composition of claim 32, wherein the composition has a compression strength of less than or equal to about 10 MPa.

* * * * *